(12) United States Patent
Stuart et al.

(10) Patent No.: US 8,163,533 B2
(45) Date of Patent: Apr. 24, 2012

(54) METHODS AND COMPOSITIONS FOR COMBINATORIAL-BASED PRODUCTION OF MULTIVALENT RECOMBINANT ANTIGENS

(75) Inventors: W. Dorsey Stuart, San Francsico, CA (US); Edward B. Cambareri, La Honda, CA (US)

(73) Assignee: Intrexon Corporation, Germantown, MD (US)

( * ) Notice: Subject to any disclaimer, the term of this patent is extended or adjusted under 35 U.S.C. 154(b) by 208 days.

(21) Appl. No.: 11/577,303

(22) PCT Filed: Oct. 17, 2005

(86) PCT No.: PCT/US2005/037249
§ 371 (c)(1),
(2), (4) Date: Nov. 30, 2007

(87) PCT Pub. No.: WO2006/044796
PCT Pub. Date: Apr. 27, 2006

(65) Prior Publication Data
US 2008/0318274 A1    Dec. 25, 2008

Related U.S. Application Data

(60) Provisional application No. 60/619,364, filed on Oct. 15, 2004.

(51) Int. Cl.
*C12N 1/15*    (2006.01)
*A61K 39/145*    (2006.01)

(52) U.S. Cl. .............. 435/254.11; 424/202.1; 424/209.1

(58) Field of Classification Search .................. None
See application file for complete search history.

(56) References Cited

U.S. PATENT DOCUMENTS

| | | | |
|---|---|---|---|
| 4,486,533 A | 12/1984 | Lambowitz | |
| 4,816,405 A | 3/1989 | Yelton et al. | |
| 4,885,249 A | 12/1989 | Buxton et al. | |
| 4,935,349 A | 6/1990 | McKnight et al. | |
| 5,643,745 A | 7/1997 | Stuart | |
| 5,683,899 A | 11/1997 | Stuart | |
| 6,268,140 B1 | 7/2001 | Stuart | |
| 2003/0092145 A1* | 5/2003 | Jira et al. | 435/173.3 |

FOREIGN PATENT DOCUMENTS

WO    WO-95/21263    8/1995

OTHER PUBLICATIONS

Buczynski et al., Fungal Genetics Newsletter (1995 Suppl.) 42A:83.
Carattoli et al., Proc Nat Acad Sci USA (1995) 92:6612-6616.
Cove, Biochim Biophys Acta (1996) 113:51-56.
Dalbey et al., TIBS (1992) 17:474-478.
Davis and De Serres, Methods Enzymol (1971) 17A:79-141.
Haas et al., Genetics (1952) 37:217-226.
Kato et al., Fungal Genetics Newsletter (1995 Suppl.) 42A:46,83.
Koo and Stuart, Genome (1991) 34:644-651.
Lambowitz et al., J Cell Biol (1979) 82:17-31.
Mackenzie et al., J Gen Microbial (1993) 139:2295-2307.
Nakano et al., Fungal Genetics Newsletter (1995 Suppl.) 40:54-56.
Peberdy, Trends in BioTechnology (1994) 12:50-57.
Perkins et al., "Chromosomal Loci of Neurospora crassa", Microbiological Reviews (1982) 46:426-570.
Stadler et al., Genetics (1966) 54:677-685.
Stuart et al., Genome (1988) 30:198-203.
Vann, Fungal Genetics Newsletter (1995 Suppl.) 42A:53.
Vollmer and Yanofsky, Proc Natl Acad Sci USA (1986) 83:4869-4873.
Yamashita et al., Fungal Genetics Newsletter (1995 Suppl.) 42A:54.
Supplementary European Search Report for EP 05808466.6, mailed Aug. 6, 2008, 6 pages.

\* cited by examiner

*Primary Examiner* — Stacy B. Chen
(74) *Attorney, Agent, or Firm* — Morrison & Foerster LLP

(57) ABSTRACT

The present invention provides methods and compositions for rapidly producing multivalent recombinant vaccines using filamentous fungal heterokaryons. The present invention relies on the use of filamentous fungal heterokaryons that are generated from combinations of two or more parent strains into which recombinant DNA molecules encoding variants of antigens derived from pathogenic organisms have been introduced. The resulting vaccines are multivalent.

4 Claims, 9 Drawing Sheets

Figure 1

Figure 7:
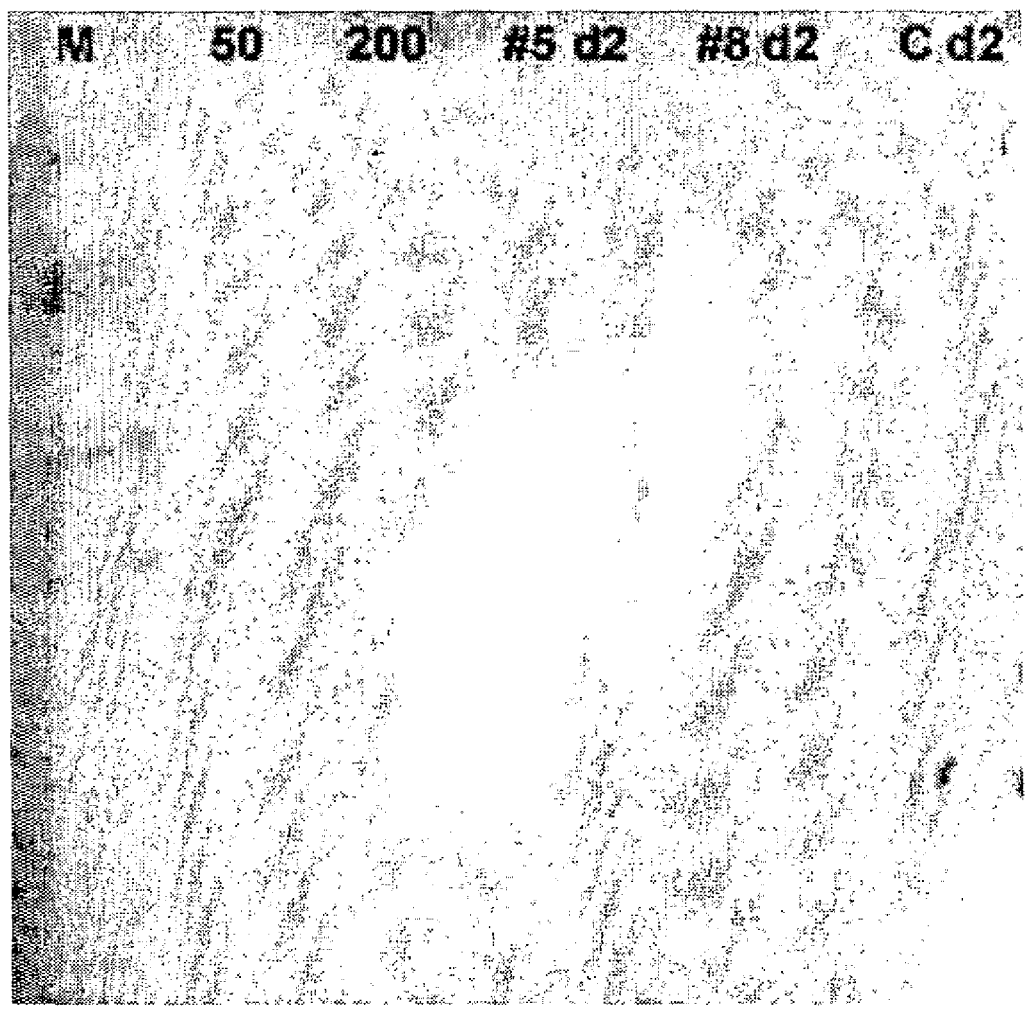

AGATCTTCGCA<u>ATG</u>AAGTTTCTTCAAGTTCTTCCAGCACTCATCCCCGCCGCGCTC
GCCCAAGACCAAATCTGCATCGGATATCATGCAAACAACTCCACCGAACAAGTCG
ATACCATTATGGAAAAGAACGTCACTGTTACCCATGCACAAGACATCCTGGAAAA
AACGCACAACGGCAAACTCTGTGACCTGGACGGGGTCAAGCCCCTTATTTTGCGC
GATTGCTCAGTCGCCGGCTGGCTCCTCGGAAACCCAATGTGCGACGAGTTTATCAA
TGTCCCCGAGTGGTCTTATATTGTTGAAAAGCCAACCCAGTGAACGATCTGTGCT
ATCCCGGCGATTTTAACGACTACGAAGAGCTCAAACACCTTCTCTCCCGTATCAAT
CACTTTGAGAAGATTCAGATCATCCCCAAGTCCTCCTGGAGCAGTCACGAGGCATC
ACTGGGCGTCAGCAGCGCCTGTCCTTATCAGGGCAAGTCCTCTTTCTTTCGCAACG
TCGTCTGGCTCATCAAGAAGAACTCCACGTACCCAACCATCAAGCGGAGCTATAA
CAACACTAACCAGGAAGACCTCCTTGTCCTGTGGGGAATCCATCATCCAAACGAC
GCAGCTGAACAGACAAAATTGTACCAGAATCCTACTACGTATATCAGCGTCGGCA
CCTCGACGTTGAACCAGCGACTTGTCCCCGAATTGCGACTCGATCCAAGGTCAAC
GGGCAATCTGGCCGCATGGAATTTTTTGGACCATCCTCAAGCCAAACGACGCCAT
CAACTTCGAATCAAATGGCAACTTCATCGCACCCGAATACGCCTACAAGATCGTG
AAAAAAGGAGATAGTACAATCATGAAGTCAGAGCTTGAATATGGCAACTGTAATA
CGAAGTGTCAAACTCCCATGGGGGCGATCAATAGCAGCATGCCTTTCCATAACATT
CACCCCCTTACTATTGGCGAATGCCCAAAATATGTCAAGTCGAATCGCCTCGTGCT
CGCAACCGGCCTTCGCAACTCTCCCCAGCGCGAAAGGAGGCGGAAGAAGCGCGGT
CTTTTCGGTGCAATCGCAGGCTTCATCGAAGGCGGATGGCAGGGCATGGTCGACG
GCTGGTACGGATACCATCACTCAAACGAACAAGGCTCTGGTTATGCAGCGGACAA
GGAATCGACACAAAAGGCAATTGACGGCGTCACCAACAAAGTTAACTCTATTATC
GACAAAATGAACACCCAATTCGAGGCCGTGGGACGTGAATTTAATAACCTCGAGC
GCCGCATCGAGAACTTGAACAAAAAGATGGAGGATGGCTTCTTGGACGTCTGGAC
TTACAATGCCGAGTTGCTCGTGCTCATGGAAAATGAAAGAACGCTCGACTTCCAC
GATTCCAACGTTAAGAACCTCTACGACAAGGTGAGACTCCAACTCCGCGACAACG
CTAAGGAGCTTGGCAACGGTTGCTTTGAGTTCTACCACAAGTGCGATAACGAATGC
ATGGAATCCGTCAGAAATGGCACCTACGACTACCCCCAATACTCCGAAGAAGCAC
GATTGAATCGCGAAGAAATTTCTGGTGTCAAACTTGAATCTATCGGAATCTACCAA
ATCCTCTCTATCTACTCAACCGTCGCTTCCTCCCTCGCCCTCGCTATCATGGTTGCC
GGTCTTTCTCTCTGGATGTGTTCAAATGGCTCCCTTCAATGTCGCTAATCTAGA

Figure 2

MKFLQVLPALIPAALAQDTICIGYHANNSTDTVDTVLEKNVTVTHSVNLLEDSHNGK
LCLLKGIAPLQLGNCSVAGWILGNPECELLISKESWSYIVETPNPENGTCYPGYFADYE
ELREQLSSVSSFERFEIFPKESSWPNHTVTGVSASCSHNGKSSFYRNLLWLTGKNGLYP
NLSKSYVNNKEKEVLVLWGVHHPPNIGNQRALYHTENAYVSVVSSHYSRRFTPEIAK
RPKVRDQEGRINYYWTLLEPGDTIIFEANGNLIAPWYAFALSRGFGSGIITSNAPMDEC
DAKCQTPQGAINSSLPFQNVHPVTIGECPKYVRSAKLRMVTGLRNIPSIQSRGLFGAIA
GFIEGGWTGMVDGWYGYHHQNEQGSGYAADQKSTQNAINGITNKVNSVIEKMNTQF
TAVGKEFNKLERRMENLNKKVDDGFLDIWTYNAELLVLLENERTLDFHDSNVKNLYE
KVKSQLKNNAKEIGNGCFEFYHKCNNECMESVKNGTYDYPKYSEESKLNREKI

Figure 3

AGATCTTCGCAATGAAGTTTCTTCAAGTTCTTCCAGCACTCATCCCCGCCGCGCTC
GCCCAAGACCAAATCTGCATCGGATATCATGCAAACAACTCCACCGAACAAGTCG
ATACCATTATGGAAAAGAACGTCACTGTTACCCATGCACAAGACATCCTGGAAAA
AACGCACAACGGCAAACTCTGTGACCTGGACGGGGTCAAGCCCCTTATTTTGCGC
GATTGCTCAGTCGCCGGCTGGCTCCTCGGAAACCCAATGTGCGACGAGTTTATCAA
TGTCCCCGAGTGGTCTTATATTGTTGAAAAAGCCAACCCAGTGAACGATCTGTGCT
ATCCCGGCGATTTTAACGACTACGAAGAGCTCAAACACCTTCTCTCCCGTATCAAT
CACTTTGAGAAGATTCAGATCATCCCCAAGTCCTCCTGGAGCAGTCACGAGGCATC
ACTGGGCGTCAGCAGCGCCTGTCCTTATCAGGGCAAGTCCTCTTTCTTTCGCAACG
TCGTCTGGCTCATCAAGAAGAACTCCACGTACCCAACCATCAAGCGGAGCTATAA
CAACACTAACCAGGAAGACCTCCTTGTCCTGTGGGGAATCCATCATCCAAACGAC
GCAGCTGAACAGACAAAATTGTACCAGAATCCTACTACGTATATCAGCGTCGGCA
CCTCGACGTTGAACCAGCGACTTGTCCCCCGAATTGCGACTCGATCCAAGGTCAAC
GGGCAATCTGGCCGCATGGAATTTTTTTGGACCATCCTCAAGCCAAACGACGCCAT
CAACTTCGAATCAAATGGCAACTTCATCGCACCCGAATACGCCTACAAGATCGTG
AAAAAAGGAGATAGTACAATCATGAAGTCAGAGCTTGAATATGGCAACTGTAATA
CGAAGTGTCAAACTCCCATGGGGGCGATCAATAGCAGCATGCCTTTCCATAACATT
CACCCCCTTACTATTGGCGAATGCCCAAAATATGTCAAGTCGAATCGCCTCGTGCT
CGCAACCGGCCTTCGCAACTCTCCCCAGCGCGAAAGGAGGCGGAAGAAGCGCGGT
CTTTTCGGTGCAATCGCAGGCTTCATCGAAGGCGGATGGCAGGGCATGGTCGACG
GCTGGTACGGATACCATCACTCAAACGAACAAGGCTCTGGTTATGCAGCGGACAA
GGAATCGACACAAAAGGCAATTGACGGCGTCACCAACAAAGTTAACTCTATTATC
GACAAAATGAACACCCAATTCGAGGCCGTGGGACGTGAATTTAATAACCTCGAGC
GCCGCATCGAGAACTTGAACAAAAAGATGGAGGATGGCTTCTTGGACGTCTGGAC
TTACAATGCCGAGTTGCTCGTGCTCATGGAAAATGAAAGAACGCTCGACTTCCAC
GATTCCAACGTTAAGAACCTCTACGACAAGGTGAGACTCCAACTCCGCGACAACG
CTAAGGAGCTTGGCAACGGTTGCTTTGAGTTCTACCACAAGTGCGATAACGAATGC
ATGGAATCCGTCAGAAATGGCACCTACGACTACCCCCAATACTCCGAAGAAGCAC
GATTGAATCGCGAAGAAATTTCTGGTGTCAAACTTGAATCTATCGGAATCTACCAA
ATCCTCTCTATCTACTCAACCGTCGCTTCCTCCCTCGCCCTCGCTATCATGGTTGCC
GGTCTTTCTCTCTGGATGTGTTCAAATGGCTCCCTTCAATGTCGCTAATCTAGA

Figure 4

MKFLQVLPALIPAALAQDQICIGYHANNSTEQVDTIMEKNVTVTHAQDILEKTHNGK
LCDLDGVKPLILRDCSVAGWLLGNPMCDEFINVPEWSYIVEKANPVNDLCYPGDFND
YEELKHLLSRINHFEKIQIIPKSSWSSHEASLGVSSACPYQGKSSFFRNVVWLIKKNSTY
PTIKRSYNNTNQEDLLVLWGIHHPNDAAEQTKLYQNPTTYISVGTSTLNQRLVPRIATR
SKVNGQSGRMEFFWTILKPNDAINFESNGNFIAPEYAYKIVKKGDSTIMKSELEYGNC
NTKCQTPMGAINSSMPFHNIHPLTIGECPKYVKSNRLVLATGLRNSPQRERRRKKRGL
FGAIAGFIEGGWQGMVDGWYGYHHSNEQGSGYAADKESTQKAIDGVTNKVNSIIDK
MNTQFEAVGREFNNLERRIENLNKKMEDGFLDVWTYNAELLVLMENERTLDFHDSN
VKNLYDKVRLQLRDNAKELGNGCFEFYHKCDNECMESVRNGTYDYPQYSEEARLNR
EEISGVKLESIGIYQILSIYSTVASSLALAIMVAGLSLWMCSNGSLQCR

Figure 5

AGATCTTCGCAATGTCTCTTCTCACTGAAGTTGAAACTTACGTGCTTTCCATCATCC
CGTCTGGTCCACTCAAAGCTGAAATCGCACAAAAACTTGAAGATGTCTTCGCCGG
CAAGAACACTGATCTCGAAGCTCTCATGGAATGGCTGAAAACGCGCCCGATTCTC
TCACCACTCACCAAGGGCATCCTCGGTTTTGTCTTTACCCTTACAGTCCCCTCAGA
ACGCGGACTCCAAAGACGTAGATTTGTGCAAAACGCCCTGAACGGTAACGGAGAC
CCTAACAATATGGACCGCGCAGTCAAGCTCTACAAAAAACTCAAGAGAGAGATTA
CTTTCCACGGTGCTAAGGAAGTTGCCCTCTCATATTCTACCGGTGCTCTCGCTTCTT
GCATGGGCCTCATTTACAACCGCATGGGAACGGTTACCACTGAAGTTGCTTTTGGC
CTTGTCTGCGCCACATGCGAACAAATTGCTGACTCTCAACATCGCTCTCATCGTCA
AATGGCCACAATCACAAACCCCCTCATCCGACACGAAAATAGAATGGTCCTCGCA
TCAACAACAGCAAAGGCTATGGAACAAATGGCAGGCTCATCAGAACAGGCAGCC
GAAGCTATGGAGATCGCAAACCAAGCCCGACAGATGGTTCAAGCTATGCGCACCA
TTGGCACTCACCCTAATTCCTCAGCAGGTCTTAGAGACAATCTCCTCGAAAATCTT
CAAGCCTACCAAAAACGAATGGGCGTCCAAATGCAACGCTTTAAATAATCTAGA

Figure 6

MSLLTEVETYVLSIIPSGPLKAEIAQKLEDVFAGKNTDLEALMEWLKTRPILSPLTKGIL
GFVFTLTVPSERGLQRRRFVQNALNGNGDPNNMDRAVKLYKKLKREITFHGAKEVAL
SYSTGALASCMGLIYNRMGTVTTEVAFGLVCATCEQIADSQHRSHRQMATITNPLIRH
ENRMVLASTTAKAMEQMAGSSEQAAEAMEIANQARQMVQAMRTIGTHPNSSAGLR
DNLLENLQAYQKRMGVQMQRFK

SEQUENCE LISTING

<160> NUMBER OF SEQ ID NOS: 6

<210> SEQ ID NO 1
<211> LENGTH: 1718
<212> TYPE: DNA
<213> ORGANISM: Artificial Sequence
<220> FEATURE:
<223> OTHER INFORMATION: Synthetic hemagglutinin 0 (HA0) gene (A/New Caledonial/20/1999/H1N1)

<400> SEQUENCE: 1

```
agatcttcgc aatgaagttt cttcaagttc ttccagcact catcccgcc gcgctcgccc      60 aagaccaaat ctgcatcgga tatcatgcaa acaactccac cgaacaagtc gataccatta     120
tggaaaagaa cgtcactgtt acccatgcac aagacatcct ggaaaaaacg cacaacggca     180
aactctgtga cctggacggg gtcaagcccc ttattttgcg cgattgctca gtcgccggct     240
ggctcctcgg aaacccaatg tgcgacgagt ttatcaatgt ccccgagtgg tcttatattg     300
ttgaaaaagc caacccagtg aacgatctgt gctatcccgg cgattttaac gactacgaag     360
agctcaaaca ccttctctcc cgtatcaatc actttgagaa gattcagatc atccccaagt     420
cctcctggag cagtcacgag gcatcactgg gcgtcagcag cgcctgtcct tatcagggca     480
agtcctcttt ctttcgcaac gtcgtctggc tcatcaagaa gaactccacg tacccaacca     540
tcaagcggag ctataacaac actaaccagg aagacctcct tgtcctgtgg ggaatccatc     600
atccaaacga cgcagctgaa cagacaaaat tgtaccagaa tcctactacg tatatcagcg     660
tcggcacctc gacgttgaac cagcgacttg tcccccgaat tgcgactcga tccaaggtca     720
acgggcaatc tggccgcatg gaattttttt ggaccatcct caagccaaac gacgccatca     780
acttcgaatc aaatggcaac ttcatcgcac ccgaatacgc ctacaagatc gtgaaaaaag     840
gagatagtac aatcatgaag tcagagcttg aatatgcaa ctgtaatacg aagtgtcaaa     900 ctccccatggg ggcgatcaat agcagcatgc ctttccataa cattcacccc cttactattg     960
gcgaatgccc aaaatatgtc aagtcgaatc gcctcgtgct cgcaaccggc cttcgcaact    1020
ctccccagcg cgaaaggagg cggaagaagc gcggtctttt cggtgcaatc gcaggcttca    1080
tcgaaggcgg atggcagggc atggtcgacg gctggtacgg ataccatcac tcaaacgaac    1140
```

```
aaggctctgg ttatgcagcg acaaggaat cgacacaaaa ggcaattgac ggcgtcacca    1200
acaaagttaa ctctattatc gacaaaatga acacccaatt cgaggccgtg ggacgtgaat    1260
ttaataacct cgagcgccgc atcgagaact tgaacaaaaa gatggaggat ggcttcttgg    1320
acgtctggac ttacaatgcc gagttgctcg tgctcatgga aaatgaaaga acgtcgact     1380 tccacgattc caacgttaag aacctctacg acaaggtgag actccaactc cgcgacaacg    1440
ctaaggagct tggcaacggt tgctttgagt tctaccacaa gtgcgataac gaatgcatgg    1500
aatccgtcag aaatggcacc tacgactacc cccaatactc cgaagaagca cgattgaatc    1560
gcgaagaaat ttctggtgtc aaacttgaat ctatcggaat ctaccaaatc ctctctatct    1620
actcaaccgt cgcttcctcc ctcgccctcg ctatcatggt tgccggtctt tctctctgga    1680
tgtgttcaaa tggctccctt caatgtcgct aatctaga                            1718

<210> SEQ ID NO 2
<211> LENGTH: 516
<212> TYPE: PRT
<213> ORGANISM: Artificial Sequence
<220> FEATURE:
<223> OTHER INFORMATION: Synthetic hemagglutinin 0 (HA0) amino acid
      sequence

<400> SEQUENCE: 2

Met Lys Phe Leu Gln Val Leu Pro Ala Leu Ile Pro Ala Ala Leu Ala
 1               5                  10                  15

Gln Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255
```

Ile Phe Glu Ala Asn Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
            275                 280                 285

Asp Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile
        515

<210> SEQ ID NO 3
<211> LENGTH: 1718
<212> TYPE: DNA
<213> ORGANISM: Artificial Sequence
<220> FEATURE:
<223> OTHER INFORMATION: Synthetic hemagglutinin (HA) gene
      (A/Vietnam/1194/2004/H5N1)

<400> SEQUENCE: 3
agatcttcgc aatgaagttt cttcaagttc ttccagcact catccccgcc gcgctcgccc     60
aagaccaaat ctgcatcgga tatcatgcaa acaactccac cgaacaagtc gataccatta    120
tggaaaagaa cgtcactgtt acccatgcac aagacatcct ggaaaaaacg cacaacggca    180
aactctgtga cctggacggg gtcaagcccc ttattttgcg cgattgctca gtcgccggct    240
ggctcctcgg aaacccaatg tgcgacgagt ttatcaatgt ccccgagtgg tcttatattg    300
ttgaaaaagc caacccagtg aacgatctgt gctatcccgg cgattttaac gactacgaag    360
agctcaaaca ccttctctcc cgtatcaatc actttgagaa gattcagatc atccccaagt    420
cctcctggag cagtcacgag gcatcactgg gcgtcagcag cgcctgtcct tatcagggca    480
agtcctcttt ctttcgcaac gtcgtctggc tcatcaagaa gaactccacg tacccaacca    540

```
tcaagcggag ctataacaac actaaccagg aagacctcct tgtcctgtgg ggaatccatc    600
atccaaacga cgcagctgaa cagacaaaat tgtaccagaa tcctactacg tatatcagcg    660
tcggcacctc gacgttgaac cagcgacttg tcccccgaat tgcgactcga tccaaggtca    720
acgggcaatc tggccgcatg gaattttttt ggaccatcct caagccaaac gacgccatca    780
acttcgaatc aaatggcaac ttcatcgcac ccgaatacgc ctacaagatc gtgaaaaaag    840
gagatagtac aatcatgaag tcagagcttg aatatggcaa ctgtaatacg aagtgtcaaa    900
ctcccatggg ggcgatcaat agcagcatgc ctttccataa cattcacccc cttactattg    960
gcgaatgccc aaaatatgtc aagtcgaatc gcctcgtgct cgcaaccggc cttcgcaact   1020
ctccccagcg cgaaaggagg cggaagaagc gcggtctttt cggtgcaatc gcaggcttca   1080
tcgaaggcgg atggcaggc atggtcgacg gctggtacgg ataccatcac tcaaacgaac   1140
aaggctctgg ttatgcagcg gacaaggaat cgacacaaaa ggcaattgac ggcgtcacca   1200
acaaagttaa ctctattatc gacaaaatga cacccaatt cgaggccgtg ggacgtgaat   1260
ttaataacct cgagcgccgc atcgagaact tgaacaaaaa gatggaggat ggcttcttgg   1320
acgtctggac ttacaatgcc gagttgctcg tgctcatgga aaatgaaaga acgtcgact   1380 tccacgattc caacgttaag aacctctacg acaaggtgag actccaactc cgcgacaacg   1440
ctaaggagct tggcaacggt tgctttgagt tctaccacaa gtgcgataac gaatgcatgg   1500
aatccgtcag aaatggcacc tacgactacc cccaatactc cgaagaagca cgattgaatc   1560
gcgaagaaat ttctggtgtc aaacttgaat ctatcggaat ctaccaaatc ctctctatct   1620
actcaaccgt cgcttcctcc ctcgccctcg ctatcatggt tgccggtctt tctctctgga   1680
tgtgttcaaa tggctccctt caatgtcgct aatctaga                           1718

<210> SEQ ID NO 4
<211> LENGTH: 566
<212> TYPE: PRT
<213> ORGANISM: Artificial Sequence
<220> FEATURE:
<223> OTHER INFORMATION: Synthetic hemagglutinin (HA)

<400> SEQUENCE: 4

Met Lys Phe Leu Gln Val Leu Pro Ala Leu Ile Pro Ala Ala Leu Ala
 1               5                  10                  15

Gln Asp Gln Ile Cys Ile Gly Tyr His Ala Asn Asn Ser Thr Glu Gln
                20                  25                  30

Val Asp Thr Ile Met Glu Lys Asn Val Thr Val Thr His Ala Gln Asp
            35                  40                  45

Ile Leu Glu Lys Thr His Asn Gly Lys Leu Cys Asp Leu Asp Gly Val
        50                  55                  60

Lys Pro Leu Ile Leu Arg Asp Cys Ser Val Ala Gly Trp Leu Leu Gly
65                  70                  75                  80

Asn Pro Met Cys Asp Glu Phe Ile Asn Val Pro Glu Trp Ser Tyr Ile
                85                  90                  95

Val Glu Lys Ala Asn Pro Val Asn Asp Leu Cys Tyr Pro Gly Asp Phe
            100                 105                 110

Asn Asp Tyr Glu Glu Leu Lys His Leu Leu Ser Arg Ile Asn His Phe
        115                 120                 125

Glu Lys Ile Gln Ile Ile Pro Lys Ser Ser Trp Ser Ser His Glu Ala
    130                 135                 140

Ser Leu Gly Val Ser Ser Ala Cys Pro Tyr Gln Gly Lys Ser Ser Phe
145                 150                 155                 160
```

```
Phe Arg Asn Val Val Trp Leu Ile Lys Lys Asn Ser Thr Tyr Pro Thr
            165                 170                 175

Ile Lys Arg Ser Tyr Asn Asn Thr Asn Gln Glu Asp Leu Leu Val Leu
        180                 185                 190

Trp Gly Ile His His Pro Asn Asp Ala Ala Glu Gln Thr Lys Leu Tyr
            195                 200                 205

Gln Asn Pro Thr Thr Tyr Ile Ser Val Gly Thr Ser Thr Leu Asn Gln
        210                 215                 220

Arg Leu Val Pro Arg Ile Ala Thr Arg Ser Lys Val Asn Gly Gln Ser
225                 230                 235                 240

Gly Arg Met Glu Phe Phe Trp Thr Ile Leu Lys Pro Asn Asp Ala Ile
            245                 250                 255

Asn Phe Glu Ser Asn Gly Asn Phe Ile Ala Pro Glu Tyr Ala Tyr Lys
        260                 265                 270

Ile Val Lys Lys Gly Asp Ser Thr Ile Met Lys Ser Glu Leu Glu Tyr
        275                 280                 285

Gly Asn Cys Asn Thr Lys Cys Gln Thr Pro Met Gly Ala Ile Asn Ser
        290                 295                 300

Ser Met Pro Phe His Asn Ile His Pro Leu Thr Ile Gly Glu Cys Pro
305                 310                 315                 320

Lys Tyr Val Lys Ser Asn Arg Leu Val Leu Ala Thr Gly Leu Arg Asn
            325                 330                 335

Ser Pro Gln Arg Glu Arg Arg Lys Lys Arg Gly Leu Phe Gly Ala
            340                 345                 350

Ile Ala Gly Phe Ile Glu Gly Gly Trp Gln Gly Met Val Asp Gly Trp
            355                 360                 365

Tyr Gly Tyr His His Ser Asn Glu Gln Gly Ser Gly Tyr Ala Ala Asp
            370                 375                 380

Lys Glu Ser Thr Gln Lys Ala Ile Asp Gly Val Thr Asn Lys Val Asn
385                 390                 395                 400

Ser Ile Ile Asp Lys Met Asn Thr Gln Phe Glu Ala Val Gly Arg Glu
            405                 410                 415

Phe Asn Asn Leu Glu Arg Arg Ile Glu Asn Leu Asn Lys Lys Met Glu
            420                 425                 430

Asp Gly Phe Leu Asp Val Trp Thr Tyr Asn Ala Glu Leu Leu Val Leu
            435                 440                 445

Met Glu Asn Glu Arg Thr Leu Asp Phe His Asp Ser Asn Val Lys Asn
            450                 455                 460

Leu Tyr Asp Lys Val Arg Leu Gln Leu Arg Asp Asn Ala Lys Glu Leu
465                 470                 475                 480

Gly Asn Gly Cys Phe Glu Phe Tyr His Lys Cys Asp Asn Glu Cys Met
            485                 490                 495

Glu Ser Val Arg Asn Gly Thr Tyr Asp Tyr Pro Gln Tyr Ser Glu Glu
            500                 505                 510

Ala Arg Leu Asn Arg Glu Glu Ile Ser Gly Val Lys Leu Glu Ser Ile
            515                 520                 525

Gly Ile Tyr Gln Ile Leu Ser Ile Tyr Ser Thr Val Ala Ser Ser Leu
            530                 535                 540

Ala Leu Ala Ile Met Val Ala Gly Leu Ser Leu Trp Met Cys Ser Asn
545                 550                 555                 560

Gly Ser Leu Gln Cys Arg
            565
```

-continued

<210> SEQ ID NO 5
<211> LENGTH: 776
<212> TYPE: DNA
<213> ORGANISM: Artificial Sequence
<220> FEATURE:
<223> OTHER INFORMATION: Synthetic M1 matrix protein
(A/Vietnam/1194/2004/H5N1)

<400> SEQUENCE: 5

```
agatcttcgc aatgtctctt ctcactgaag ttgaaactta cgtgctttcc atcatcccgt     60
ctggtccact caaagctgaa atcgcacaaa aacttgaaga tgtcttcgcc ggcaagaaca    120
ctgatctcga agctctcatg gaatggctga aaacgcgccc gattctctca ccactcacca    180
agggcatcct cggttttgtc tttaccctta cagtcccctc agaacgcgga ctccaaagac    240
gtagatttgt gcaaaacgcc ctgaacggta acggagaccc taacaatatg gaccgcgcag    300
tcaagctcta caaaaaactc aagagagaga ttactttcca cggtgctaag gaagttgccc    360
tctcatattc taccggtgct ctcgcttctt gcatgggcct catttacaac cgcatgggaa    420
cggttaccac tgaagttgct tttggccttg tctgcgccac atgcgaacaa attgctgact    480
ctcaacatcg ctctcatcgt caaatggcca caatcacaaa ccccctcatc cgacacgaaa    540
atagaatggt cctcgcatca acaacagcaa aggctatgga acaaatggca ggctcatcag    600
aacaggcagc cgaagctatg gagatcgcaa accaagcccg acagatggtt caagctatgc    660
gcaccattgg cactcaccct aattcctcag caggtcttag agacaatctc ctcgaaaatc    720
ttcaagccta ccaaaaacga atgggcgtcc aaatgcaacg ctttaaataa tctaga        776
```

<210> SEQ ID NO 6
<211> LENGTH: 252
<212> TYPE: PRT
<213> ORGANISM: Artificial Sequence
<220> FEATURE:
<223> OTHER INFORMATION: Synthetic M1 protein

<400> SEQUENCE: 6

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175
```

```
Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250
```

METHODS AND COMPOSITIONS FOR COMBINATORIAL-BASED PRODUCTION OF MULTIVALENT RECOMBINANT ANTIGENS

CROSS-REFERENCE TO RELATED APPLICATIONS

This application is the national phase under 35 U.S.C. §371 of PCT International Application No. PCT/US2005/037249, filed Oct. 17, 2005, which designates the United States of America, which claims the benefit of priority of U.S. Patent Application No. 60/619,364, filed Oct. 15, 2004. The disclosure of these applications are incorporated by reference in their entirety.

RELATED APPLICATION

This application relates to U.S. Provisional Application No. 60/619,364, filed Oct. 15, 2004, which is hereby incorporated by reference in its entirety.

Reference to Sequence Listing Submitted Via EFS-Web

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 2389182001400Seqlist.txt | Nov. 17, 2005 | 17,253 bytes |

TECHNICAL FIELD

The disclosed invention relates to the field of molecular biology and the production of multivalent vaccines against pathogenic organisms. One embodiment of the invention specifically provides methods and compositions that provide a population of antigen encoding nucleotide sequences in heterokaryotic filamentous fungi that can be use to produce a population of multivalent vaccines.

BACKGROUND ART

Vaccines are currently produced by a variety of methods. Typically, influenza vaccines are produced using fertilized chicken eggs. In the United States, the Centers for Disease Control will select three virus strains which are thought to represent the most likely viruses to strike in a particular flu season. Samples of the selected viruses are provided to manufacturers as seed virus stocks which possess the desired antigenic characteristics. The seed viruses are injected into fertilized chicken eggs. These eggs are incubated while the influenza viruses multiplies. After a suitable period of time the eggs are opened and the egg white is harvested. This sample contains the viruses. The viruses are purified from the egg material and inactivated. The individual virus stocks are then combined to create the common influenza vaccine, which is typically a trivalent vaccine.

There are a variety of problems which can occur which can compromise an entire vaccine batch. For example, problems with sterility lead to the decertification of Chiron's vaccine production facility in 2004. This situation illustrates how unreliable traditional vaccine production methods can be.

Moreover, current influenza vaccine production methods employ the use of hundreds of millions of chicken eggs each year. The storage, handling, and processing steps are time consuming and labor intensive. Additionally, given the long production times, if the if a new strain of influenza virus became predominant during a flu season, current egg based production methods would take several months for a new vaccine to be produced.

In view of these limitations, a more flexible and efficient method of producing antigenic material, such as an influenza vaccine is sorely needed.

Recombinant Fungal Expression of Proteins

The cloning and expression of heterologous genes in fungi has been used to produce a variety of useful proteins. For example: Lambowitz, U.S. Pat. No. 4,486,533, discloses the autonomous replication of DNA vectors for filamentous fungi by mitochondrial plasmid DNA and the introduction and expression of heterologous genes into *Neurospora*; Yelton et al., U.S. Pat. No. 4,816,405, discloses tools and systems that enable the modification of important strains of filamentous ascomycetes to produce and secrete large quantities of desired heterologous proteins; Buxton et aL, U.S. Pat. No. 4,885,249, discloses the transformation of *Aspergillus niger* by a DNA vector that contains a selectable marker capable of being incorporated into the host *A. niger* cells; and McKnight et al., U.S. Pat. No. 4,935,349, discloses a method for expressing higher eukaryotic genes in *Aspergillus* involving promoters capable of directing the expression of a heterologous gene in *Aspergillus* and other filamentous fungi. Similar techniques have been used to clone the mtr gene involved with amino acid transport in *Neurospora crassa* ("*N. crassa*") and to verify the tight linking of the cloned DNA to genomic markers flanking this gene in vivo. Stuart, W. D. et al., Genome (19&9) 30:198-203; Koo, K. and Stuart, W D. Genome (1991) 34:644-651.

Filamentous fungi possess many characteristics which make them good candidates for use in producing eukaryotic proteins. Filamentous fungi can secrete complex proteins; correctly fold three dimensional proteins including disulfide bond formation; proteolytically clip proteins following translation; and glycosylate proteins using n-linked and o-linked glycosylation reactions. These abilities have made this group of organisms attractive hosts for the production of secreted recombinant proteins. (MacKenzie, D. A. et al., J Gen Microbial (1993) 139:2295-2307; Peberdy, J. F., Trends in Bio-Technology (1994) 12:50-57).

*Neurospora crassa* has been used as a host cell for recombinant homologous and heterologous protein production. (Carattoli, A., et al., Proc Nat Acad Sci USA, (1995) 92:6612-6616; Yamashita, R. A. et al., Fungal Genetics Newsletter (1995 Suppl.) 42A; Kato, E. et al., Fungal Genetics Newsletter (1995 Suppl.) 42A; Buczynski, S. et al. Fungal Genetics Newsletter (1995 Suppl.) 42A, Nakano, E. T. et al. Fungal Genetics Newsletter (1995 Suppl.) 40:54 0). In addition, *Neurospora crassa* has been used as a host cell for expressing recombinant heterodimeric and multimeric proteins by means of a heterokaryon, U.S. Pat. No. 5,643,745 July, 1997, Stuart 435/69.1.

SUMMARY OF THE INVENTION

The present invention provides heterokaryon filamentous fungus that produce multivalent vaccines.

The individual heterokaryons of the present invention are generated by fusing a first, and a second, and, in the case of trivalent vaccines, a third parent fungal strain and, in the case of higher levels of vaccine valences, one additional parent strain for each set of antigens added, each parent strain containing the necessary markers to maintain a heterokaryotic state as well as an expression unit that encodes a naturally occurring variant of an antigen of a multivalent vaccine, a rationally designed variant of an antigen of a multivalent vaccine, or a randomly generated variant of an antigen of a multivalent vaccine. Thus, in addition to natural variants, variants, generated through the use of chemical, physical or site-directed mutagenesis or other techniques can be produced.

The heterokaryons of the present invention are useful for selectively producing desired multivalent vaccines of defined antigens.

Based on the above, the present invention provides heterokaryons that produce variants of multivalent vaccines.

BRIEF DESCRIPTION OF THE DRAWINGS

FIG. 1 shows the nucleotide sequence (SEQ ID NO:1) of synthetic hemagglutinin 0 (HA0) gene (A/New Caledonial/20/1999/H1N1) and conceptual translation for fungal expression. The initiation codon is underlined.

FIG. 2 shows the amino acid sequence (SEQ ID NO:2) encoded by the synthetic hemagglutinin 0 (HA0) gene. The fungal signal sequence is shown in bold.

FIG. 3 shows the nucleotide sequence (SEQ ID NO:3) of synthetic hemagglutinin (HA) gene (A/Vietnam/1194/2004/H5N1). The initiation codon is underlined.

FIG. 4 shows the amino acid sequence (SEQ ID NO:4) encoded by the synthetic hemagglutinin (HA) gene. The fungal signal sequence is shown in bold.

FIG. 5 shows the nucleotide sequence (SEQ ID NO:5) of synthetic M1 matrix protein (A/Vietnam/1194/2004/H5N1). The initiation codon is underlined.

FIG. 6 shows the amino acid sequence (SEQ ID NO:6) encoded by the M1 gene.

FIG. 7 shows a western blot detection of expression of the synthetic HAO in *N. crassa*. Medium from 2 day shake-flask cultures of strains HAO5 and HAO8, as well as untransformed Control (C), and 50 and 200 ng of control HA (A/New Caldonia 20/99, Protein Sciences), were fractionated by SDS PAGE and blotted to nitrocellulose. Haemagglutinin was detected using a goat polyclonal anti-HA (H1N1) antibody (BioDesign), followed by anti-goat Ig-alkaline phosphatase conjugate and colorimetric detection.

FIG. 8 shows a Coomassie brilliant blue stained gel of medium from 2 day shake-flask cultures of HAO5 and HAO8. Relatively little secreted protein is produced by 2 days in shake-flasks under these conditions.

FIG. 9 shows static-culture expression of HAO5. Western blot of medium from a 6 day static culture of HAO5. HA proteins were detected as above in FIG. 7. In this experiment, the major detected band is at ~57 kDa (the predicted size based on amino acid composition), versus 72 kDA for the control HA protein (C).

DISCLOSURE OF THE INVENTION

A "heterokaryon" (or a heterokaryotic cell) is a cell formed from the fusion of two (or more) filamentous fungal parent strains, each heterokaryon cell thus containing two (or more) genetically different nuclei. Heterokaryons contain nuclei from parent strains that are generally homozygous for all heterokaryon compatibility alleles (except for the mating type allele when the tol gene is present). At least ten chromosomal loci have been identified for heterokaryon incompatibility: het-c, het-d, het-e, het-i, het-5, het-6, het-7, het-8, het-9 and het-10, and more are inferred to exist. Peris et al., "Chromosomal Loci of *Neurospora crassa*", Microbiological Reviews (1982) 46:426-570, at 478.

The present invention advances the work of that disclosed in U.S. Pat. Nos. 5,643,745, 5,683,899 and 6,268,140 by providing methods and compositions for producing a population of multivalent vaccines using heterokaryotic filamentous fungi. Such methods and compositions are useful in the discovery and production of multivalent vaccines, such as antiviral vaccines, antibacterial vaccines and antifungal vaccines.

DESCRIPTION OF THE PREFERRED EMBODIMENTS

The present invention provides novel methods and compositions for generating a population of multivalent vaccines. The multivalent vaccines are generated from an ordered or a random combination of defined antigens. To obtain a multivalent vaccine, a heterokaryon is obtained in a method comprising the steps of introducing a first, a second, and sometimes a third or more populations of DNA molecules that encode defined antigens of a multivalent vaccine into a first, a second fungal and sometimes a third or more host parents, forming heterokaryotic fungal strains using the first, second and sometimes third or more host fungal parents, and then, if appropriate, culturing the resulting heterokaryon under conditions in which the subunit encoding DNAs are expressed and further screening the resulting heterokaryons for the production of a multivalent vaccine having the desired properties. Each of the elements, namely the fungal parents, the DNA molecules and the fusion methods are described in detail below.

Nature of Filamentous Fungi and Background Requirements for Heterokaryon Formation Fungi can occur in single mononucleated cells that yield filamentous multinuclear strands, yeast cells, fruiting bodies with diverse spores, and/or cells that are differentiated sexually. They can also exist in multinucleated forms. The principal element of the growing form of a fungus as a mold is the hypha, a branching tubular structure, about 2 μm-10 μm in diameter. Hyphae grow by elongation at their tips (apical growth) and by producing side branches. Thus, as a colony grows, its hyphae form a mass of intertwining strands.

Some hyphae penetrate into the culture medium on which the fungus is growing to absorb nutrients, while those hyphae that project above the surface of the medium constitute an "aerial mycelium." Most colonies grow at the surface of liquid or solid media as irregular, dry, filamentous mats. In most species, the hyphae are divided by cross-walls called "septa." These septa, however, have fine, central pores. Thus, even septate hyphae have nuclei that are embedded in a continuous mass of cytoplasm and, in effect, contain a multiplicity of nuclei in a transportable cytoplasm.

The term "filamentous fungi" refers to those fungi that can form a mycelium through a mass of branching, interlocking filaments and, although interrupted by cross walls, permit the passage of cytoplasm between compartments due to perforations in the cross walls. Many of these fungi form meiotic spores within a sac when propagated sexually. With the appropriate stimulation, however, the mechanism of which is not entirely understood, reproduction can occur asexually. In this manner of reproduction, spores known as "conidia" are borne externally at the tips of budding projections formed at various locations along the filaments.

The filamentous fungi used to generate the heterokaryon panels of the present invention are generally Phycomycetes, Ascomycetes, Basidiomycetes, and Deuteromycetes. The Phycomycetes include all non-septate, as well as some septate, filamentous fungi. Their asexual spores are of various kinds and include sporangiospores contained within sacs formed at the end of specialized stalks. Different species have different sexual cycles.

Ascomycetes are distinguished from other fungi by the ascus, a saclike structure containing sexual spores, known as ascospores. The ascospores are the end product of mating, the fusion of male and female nuclei, two meiotic divisions, and usually one final mitotic division. Basidiomycetes are distinguished by sexual spores that form on the surface of a specialized structure. The Deuteromycetes are often referred to as "imperfect fungi" because no sexual phase has yet been observed. Their hyphae are septate, and conidial forms are similar to those of the Ascomycetes.

The preferred filamentous fungus is of the group Ascomycetes, more preferably, from the genera *Neurospora, Aspergillus, Fusarium, Tricoderma, Chrysosporium,* and *Penicillium.* Particularly useful species from *Neurospora* include *N. intermedia, N. crassa, N. sitopula,* and *N. tetraspora,* of which the most preferred species is *N. crassa.* Useful species of *Aspergillus* include *A. nidulans, A. niger, A. terreus,* and *A. fumegatus.*

The vegetative growth of filamentous fungi involves nuclear division with cell division (mitosis). This type of cell division consists of asexual reproduction, i.e., the formation of a new clone without the involvement of gametes and without nuclear fusion by way of conidia. For example, the species of *Neurospora* contain in their nuclei seven different chromosomes, each having a single copy, i.e., the vegetative organism is haploid. This haploid state is typically maintained during mycelial growth and during asexual reproduction through the formation of conidia.

Sexual reproduction can also occur, and then two haploid cells (hyphae or conidia) of different mating type fuse to form a dikaryotic cell containing two distinct nuclei. The two haploid nuclei thus coexist in the same cytoplasm and, for a time, divide more or less in synchrony. If a cell initiates ascospore formation, however, the two different haploid nuclei can actually fuse to form a diploid nucleus, which contains pairs of homologous chromosomes. This diploid cell then begins meiosis.

A "heterokaryon" (or a heterokaryotic cell) is a cell with two (or more) genetically different nuclei. The heterokaryons of the invention must contain nuclei from cells that are homozygous for all heterokaryon compatibility alleles (except for the mating type allele when the tol gene is present). In *Neurospora* for example, at least ten chromosomal loci have been identified for heterokaryon incompatibility: het-c, het-d, het-e, het-i, het-5, het-6, het-7, het-8, het-9 and het-10, and more are inferred to exist. Perkins et al., "Chromosomal Loci of *Neurospora crassa*", Microbiological Reviews (1982) 46:426-570, at 478.

If two strains carry different alleles at one or more het loci, they are unable to form stable heterokaryons. Protoplasmic killing occurs after fusion of unlike hyphae or after microinjection of cytoplasm or extracts into unlike strains. When duplications (partial diploids) are heterozygous for het one or more alleles, growth is inhibited and highly abnormal. A number of heterokaryon incompatibility loci (specifically, het-c, -d, -e, and -i) were first defined by heterokaryon tests. Het-5 through -10 loci were detected by using duplications, as differences at het loci are common in natural populations. Id.

Mating type alleles "A" and "a" also act as het genes in *N. crassa,* although some slow heterokaryotic growth may occur. Microinjection experiments have implicated proteins in the killing reaction. Thus, opposite mating types are also generally important for the complex events associated with the proliferation of heterokaryotic aseogenous hyphae. Id. at 436 and 478. However, if the tol gene is present, the vegetative (heterokaryon) incompatibility associated with opposite mating type alleles A and a is suppressed without sexual compatibility being affected. Thus, (tol; A+a; a) heterokaryons can be fully compatible and stable if the other het loci are of the same allele (or conallelic) and A/a duplications grow normally when the tol gene is present.

If hyphae from two different strains that are conallelic for the compatibility loci are provided, they may fuse when grown in the same medium, in particular when fusion is forced as described below. The resulting culture will then contain nuclei from both strains circulating in the shared cytoplasm of a common mycelial mat.

Construction of Expression Units Encoding a Mixed Population of Defined Antigens In describing the invention, the following terminology will be used in accordance with the definitions set out below:

The invention involves the production of "heterologous multivalent vaccines" in the filamentous fungal heterokaryon. In this context, "heterologous" means that the protein is not ordinarily produced by the fungus. "Multivalent" means that the ultimate vaccine product is made up of at least two antigens or antigen variants. The product may be a heteromultivalent vaccine, comprised of entirely different antigens or can be homomultivalent, made up of variants of a single subunit. Examples of multivalent vaccines include, but are not limited to, mixtures of recombinant antigens from cell surfaces, viral coat proteins, specific pathogenic protein antigens, and the like.

A "nucleotide sequence encoding an antigen" is that portion of a sequence for which the transcript is translated into a polypeptide when operably linked to appropriate control sequences. The boundaries of the coding sequence are determined by a start codon at the 5'(amino) terminus and a translation stop codon at the 3'(carboxy) terminus. This coding sequence can be derived from, for example, prokaryotic genes, cDNA from eukaryotic mRNA, genomic DNA sequences from eukaryotic DNA (such as fungal), or may include synthetic DNA. A polyadenylation signal and transcription termination sequence will usually be located 3' to the coding sequence.

A coding sequence is "operably linked to" control sequences when the control sequences effect the expression of the coding sequence in the appropriate host cell.

An "expression unit" is a DNA molecule that contains a coding sequence operably linked to a "control sequence or region" that directs the transcription and translation of the operably linked sequence in an appropriate host organism under appropriate conditions.

A cell has been "transformed" by exogenous DNA when such exogenous DNA has been introduced into the host cell membrane. For prokaryotes such as bacteria the exogenous DNA may be maintained on an episomal element such as a plasmid. Because filamentous fungi do have nuclei (are eukaryotic), most stably transformed fungus host cells contain the exogenous DNA integrated into a chromosome, so that it is inherited by daughter cells through chromosome replication.

A "recombinant host" refers to cells that have been, are or will be transformed with DNA sequences prepared by recombinant techniques, and includes the cell originally transformed and cultures and progeny thereof.

A variety of methods can be employed to generate a population of DNA molecules that encode 1) naturally occurring variants of an antigen subunit of a multivalent vaccine, 2) randomly generated or selected variants of an antigen of a multivalent vaccine, or 3) rationally designed or selected variants of an antigen of a multivalent vaccine. In the following, an influenza vaccine is used as an illustrative example. A skilled artisan can readily use the methods outlined below, or an equivalent method known in the art, to generate the population of subunit encoding DNA molecules.

A population of DNA molecules that encode naturally occurring variants of an antigen of an antigen having natural heterogeneity can be produced using standard cDNA generation/cloning techniques. In general, a population of mRNA or viral genomic RNA is first isolated from the pathogen, or for example, in the case of influenza vaccines, directly from the genomic RNA of the virus itself. The isolated population of RNA molecules is then used as a template for the generation of cDNA molecules in art-known cloning methods such as RTPCR. The populations of cDNA molecules thus produced can be inserted into a suitable expression unit as described below.

Alternatively, for antigens whose protein sequence is know, an artificial cDNA sequence can be generated using methods known to the art, said sequence incorporating codons which are used in high frequency by the filamentous fungal host strain to produce its own endogenous proteins.

In addition, site directed or random mutagenesis can be performed on an isolated or artificial cDNA molecule that encodes an antigen of a multivalent vaccine to produce non-naturally occurring variants of the particular subunit. Procedures such as random or site-directed mismatched PCR priming, linker-scanning mutagenesis, or chemical and physical mutagenesis can readily be used to generate a population of DNA molecules that encode rationally designed or randomly generated variants of an antigen. For example, randomly generated or rationally designed PCR primers can be used to generate random or targeted heterogeneity in an antigen encoding sequence.

As used herein, a variant is said to be rationally designed when a selection criterion, such as protein folding or selecting a particular target residue or region, is used in generating the variant or selecting the variant-encoding DNA molecules. A variant is said to be randomly generated when a selection criterion is not used when generating or selecting the variant-encoding DNA molecules.

The preferred target site for generating heterogeneity in a multivalent vaccine subunit is the immunogenic epitope and surrounding amino acid sequences. In the case of the influenza antigen genes this type of creation of variation would center on the known naturally variable regions of each antigen. As an example, one could change each amino acid in the variable region one by one to produce a library of known variation.

Construction of Expression Units Encoding Antigens of the Multivalent Vaccine

The expression units containing a nucleotide molecule encoding an antigen of a multivalent vaccine are constructed using well known techniques. In general, an expression unit is generated by placing the subunit coding sequences into operable linkage with control sequences that directs the expression of the subunit encoding sequences in the ultimate filamentous fungus host.

A variety of control elements are presently known in the art for directing the expression of an operably linked protein encoding sequence in either a constitutive or inducible fashion. The choice of a control sequence will be based on the fungal strain used, conditions employed for culturing the fungus, the level of protein expression desired, and the nature of expression required (for example, inducible versus constitutive). A skilled artisan can readily utilize art-known control sequences for generating the expression units used in the present heterokaryon panel.

In addition to sequences that direct the transcription and translation of the protein-encoding sequence, the expression units of the present invention may further control signal sequences, expression control elements that direct the export of an antigen outside the cell. A review of secretory signals that are known in filamentous fungus are provided by Dalbey R. E., et al., TIBS 17:474-478 (1992). The skilled artisan can readily generate expression units that contain secretory signals.

Another form of expression unit of the present invention may contain a fusion protein that directs the antigen to the cell membrane via fusion to a host cell or heterologous membrane anchor sequence or to the cell surface by fusion to a host cell or heterologous cell surface molecule.

In one application, recombination units are generated instead of the expression units. In such a use, the subunit encoding sequence, or fragment of an antigen encoding sequence, is flanked by regions of DNA that contain sequences that are homologous to an integration site in the host fungal strain. The homologous sequences are then used to stimulate and direct homologous recombination between the recombination units and the host chromosome. When recombination units are used, the host strain is preferably first transformed with an expression unit that contains an expression control element followed by sequences that are used for targeted recombination. For example an influenza antigen can be introduced into a host fungus and then homologous recombination units can be used to introduce heterogeneity within a targeted region of the host chromosome.

Intermediate hosts are sometimes used to produce intermediate vectors capable of transforming the ultimate fungal cells. The intermediate bacterial transformants can then be grown to obtain the desired quantities of DNA, which can be used to transform a desired filamentous fungus host. Examples of commonly available bacterial vectors that can serve as intermediate vectors include, for example, pBR322, pUC8 and pUC9. Additional useful intermediate vectors include pHY201, pKBY2, pTZ18R, pX182 and pCVN2.9, pN807, pN846.

In another embodiment, the antigen or antigens or interest are expressed as a fusion protein with a fungal hydrophobin, such as EAS. Fungal hydrophobins are typically expressed and secreted in large quantities. The surfaces of the fungi are then coated with the hydrophobins. These proteins are also known to aggregate in solution. This aggregation feature allows for the preparation of aggregated recombinant proteins, which form antigenic particles. These proteins can be purified and used as antigens. When multiple antigens are expressed in the same culture, multivalent antigenic particles are produced.

It will be understood that this description and disclosure of the invention is intended to cover all embodiments that are within the spirit and scope of the invention. For example, it is within the knowledge of the art to insert, delete or substitute amino acids within the amino acid sequence of an open reading frame without substantially affecting the antigenicity of the molecule, and such multivalent antigens as can be generated with deletions, additions or substitutions to the naturally occurring subunit are included in the invention.

Nature of the Parent Strains

Since each of the parent fungal strains used in making the heterokaryons of the present invention will contain a member of a population of DNA molecules that encodes an antigen of a multivalent vaccine, one fungal parent will have a nucleus modified to contain a member of a first population of DNA molecules that encodes a first antigen or groups of antigens of a desired multivalent vaccine and each successive fungal parent will have a nucleus modified to contain a member of a different population of DNA molecules that encodes a different antigen or groups of antigens of a desired multivalent vaccine. For example, to produce a heterokaryon producing a divalent influenza vaccine, one fungal parent will produce an antigen group from cDNA from influenza type A H1 N1 while the other fungal parent will produce an antigen group from cDNA from influenza type A H3 N2. To produce a trivalent influenza vaccine one fungal parent will produce an antigen group from cDNA from influenza type A H1 N1, the second fungal parent will produce an antigen group from cDNA from influenza type A H3 N2 and the third fungal parent will produce an antigen group from cDNA from influenza type B H N. Nucleotide and protein sequence are publicly available. For example, exemplary sequences for HA genes include H3N2 (AY738729), Influenza A virus (A/Leningrad/54/1 (H1N1)) neuraminidase gene (M38309), Influenza A virus (A/Swine/Ontario/42729A/01 (H3N3)) neuraminidase (NA) gene (AY619975), Influenza A virus (A/Swine/Ontario/K01477/01 (H3N3)) neuraminidase (NA) gene (AY619966), Influenza A virus (A/Swine/Saskatchewan/18789/02 (H1N1)) neuraminidase (NA) gene (AY619960), Influenza A virus (A/Puerto Rico/8/34/Mount Sinai (H1N1)) segment 6 (NC 004523), Influenza A virus (A/mallard/Alberta/211/98 (H1N1)) neuraminidase (NA) gene (AY633214), Influenza A virus (A/mallard/Alberta/99/91 (H1N1)) neuraminidase (NA) gene (AY207541), and Influenza A virus (A/duck/Miyagil/9/77 (H1N1)) neuraminidase (NA) gene (AY207534).

In addition to having been modified to contain a DNA molecule encoding the antigen or antigen group, as described above, the nuclei of each of the parent strains must contain a genome that results in a characteristic that renders the fungus dependent on the presence of a second nucleus, and/or a third nucleus and/or additional nuclei for survival under the conditions used to form the heterokaryon. Thus, the nucleus of each parent confers a characteristic which would result in the failure of the fungus in which it is contained to survive under the culture conditions unless the second nucleus, and/or third nucleus and/or additional nuclei are also present. For example, a parent that requires a particular nutrient may be cultured on a medium lacking the nutrient along with a parent that does not have this requirement. If hyphal fusion occurs, the nucleus of the second parent confers ability to survive in the absence of this nutrient. The second parent, in turn, may require a different nutrient, not required by the first. Only fungi containing both nuclei can then survive when both nutrients are lacking.

The required nutrient can be any substance which the fungus strain cell needs for growth or which, when absent, seriously impairs the ability of the fungus strain to grow or survive. Examples of useful nutrient requirements and the relevant mutants include:

(1) amino acids such as histidine (his-1 through -7 mutants), proline (aga mutants), arginine (arg-11 mutants), citrulline (arg-11 mutants), asparagine (asn mutants), choline (chol-1 and chol-2 mutants), cysteine (cys-1 mutants), glutamine (gln-1 mutants), leucine (leu-1 through -4), lysine (lys-2, -4 and -5), methionine (mac mutants and met-6, -9 and -10 mutants), and threonine (thr-2 and -3 mutants);

(2) mixtures of aromatic amino acids, such as a mixture of p-aminobenzoic acid, tyrosine, tryptophan, and phenylalanine (required by all aro strains except aro-6, aro-7 and aro-8), a mixture of tryptophan and phenylalanine (required for aro-6 mutants), a mixture of isoleucine and valine (required for ilv-1, -2 and -3), and a mixture of phenylalanine and tyrosine (required for pt mutants);

(3) vitamins such as pantothenic acid (pan-1 mutants) and thiamine (thi-2 and thi-4 mutants);

(4) purine bases such as adenine (ad-2 through ad-4 and ad-8 mutants), hypoxanthine (ad-2 and ad-3 mutants), inosine, and guanine or guanosine (gua-1 or -2 mutants);

(5) pyrimidine bases such as uracil (pyr-1 through pyr-6);

(6) saturated fatty acids (cel mutants) or unsaturated fatty acids such as $C_{16}$ or $C_{18}$ fatty acids having a double bond in the cis conformation at either the 9- or 11-position, fatty acids with a double bond in the trans configuration at the 9-position, and fatty acids with multiple cis double bonds interrupted by methylene bridges (ufa-1 and -2);

(7) physiologically important ions such as potassium (trk);

(8) sugar alcohols such as inositol (acu mutants and inl mutants) and glycerol; and (9) other organic entities such as acetate (ace mutants), I-ketoglutarate, succinate, malate, formate or formaldehyde (for mutants), p-aminobenzoic acid (pab-1, -2 and -3 mutants), and sulfonamide (sfo mutants at 35° C.).

One specific example based on a nutritional requirement is the Arg B+gene coding for the enzyme ornithine transcarbamylase. This enzyme is present in wild type *A. niger*. Mutants lacking this enzyme (Arg B− strains) can be prepared by usual non-specific techniques, such as treatment with ultraviolet radiation, followed by screening based on an inability to grow on minimal medium, coupled with an ability to grow on a medium containing arginine. Fungi containing this genome will grow on minimal medium if they also include an Arg B+ nucleus.

Also useful for forcing heterokaryon formation are genes conferring a resistance to any one of a variety of cytotoxic agents. For example, in an alternative embodiment, one of the parents can have a requirement for a nutrient as well as a resistance to a toxic effect induced by a noxious chemical, an antibiotic or virus, or a harsh environmental conditions such as a predetermined temperature range to which the other parent is sensitive.

Specific examples of noxious chemicals that can exert a toxic effect include acriflavine (resistance conferred by acr generally, with the presence of the shg gene being required for resistance by acr-4 and acr-6); 3-amino-1,2,4-triazole (resistance conferred by acr-2, atr-1, cpc, leu-1 or leu-2)); dyes such as malachite green (resistance conferred by acr-3); caffeine (resistance conferred by caf-1); purine analogs (resistance to 8-azaadenine and 2,6-diaminopurine conferred by aza-1; resistance to 8-azaadenine and 8-azaguanine conferred by aza-2; resistance to 8-azaguanine and 6-mercaptopurine conferred by aza-3; resistance to 6-methylpurine conferred by mep(3) and mep(10); cyanide (insensitivity conferred by cni-1 in the first 24 hours of growth); tetrazolium (resistance conferred by cya-6 and cya-7); cycloheximide (resistance conferred by cyh-1, -2 and -3); chromate (resistance conferred by cys-13); 2-deoxy-D-glucose (resistance conferred by $dgr^-$); edeine (resistance conferred by edr-1 and -2); ethionine (resistance conferred by eth-1, by nap in the presence of p-fluorophenylalanine, and by oxD if the ethionine is in the D form); fluoro compounds such as 5-fluorodeoxyuridine, 5-fluorouracil, and 5-fluorouridine (resistance to all three conferred by fdu-2; resistance to 5-fluorouracil being conferred by uc-5 in an ammonia-free minimal medium; resistance to 5-fluorodeoxyuridine and 5-fluorouridine being conferred by ud-1), and fluorophenylalanine (resistance conferred by fpr-1 through -6 under certain conditions); 8-azaadenine (resistance conferred by mts); methyl methane sulfonate (insensitive or marginally sensitive for upr-1); surface-active agents such as dequalinium chloride, cetyltrimethyl ammonium bromide, and benzalkonium chloride (resistance conferred by sur-1); and metal ions such as vanadate (resistance conferred by van).

Examples of antibiotics typically exerting a toxic effect include benomyl>methyl-1-(butylcarbamolbenzimidazol-2-yl carbamate! (resistance conferred by Bml); antimycin A (insensitivity conferred by cni-1 in the first 24 hours of growth); polyene antibiotics such as nystatin (resistance conferred by erg-1 and 3); and oligomyein (resistance conferred by oli).

Also useful are genes conferring resistance to extremes in various environmental conditions such as a high or low temperature, the lack of oxygen (resistance conferred by an), constant light (resistance conferred by lis-1, -2 and -3) or the absence of light, UV radiation, ionizing radiation, and high or low osmotic pressures. In a particularly preferred embodiment, the resistance to a toxic effect is a resistance to an antibiotic such as hygromycin.

Strains generally useful in the invention can be grown on 1× Vogel's Minimal Medium (N medium) in cotton-plugged test robes, with supplements being added depending on the phenotype of the strain, such as, for example, histidine, arginine and/or inositol. Typical stains may be obtained, for example, from the Fungal Genetics Stock Center ("FGSC") and from D. D. Perkins, Stanford University. Another *N. crassa* strain believed to be useful is M246-89601-2A (obtained from Dr. Mary Case, University of Georgia, Athens). This strain is a derivative of wild-type 74A, which contains a stable qa-2 mutation (M246), an arom-9 mutation (M6-11), and an inos (io601) mutation. The double mutant qa-2, arom-9, lacks both the biosynthetic and catabolic dehydroquinase activities and is unable to grow on minimal medium without a supplement of aromatic amino acids, such as, for example, phenylalanine at a concentration of about 80 μg per ml.

Useful strains of *A. niger* (ATCC 46951) are also available from the Fungal Genetics Stock Center, as well as strains of *Fusarium, Gelasinospora*, and *Sordaria fimicola*, or can be prepared by mutagenizing with UV light to form an isolate that requires ornithine or arginine for growth in a defined minimal media. This strain, which lacks ornithine carbamoyl transferase, has been called arg B (350(–)52). Media for growing *A. niger* or *A. nidulans* are described by Cove, Biochim Biophys Acta (1966) 113:51-56.

Standard procedures are generally used for the maintenance of strains and the preparation of conidia (Davis and de Serres, Methods Enzymol (1971) 17A:79-141). Mycelia are typically grown in liquid cultures for about 14 hours (25° C.), as described in Lambowitz et al. J Cell Biol (1979) 82:17-31. Host strains can generally be grown in either Vogel's or Fries minimal medium supplemented with the appropriate nutrient(s), such as, for example, histidine; arginine; phe, tyr, and/or trp (each about 80 μg per ml); p-aminobenzoic acid (about 2 μg per ml); and inositol (about 0.2 mg per ml).

Many fungal strains with the desired characteristics are publicly available. If not readily available, however, one of ordinary skill in the art can use selection techniques well-known in the art for separating out either the desired mutants or the engineered nuclei providing the desired characteristic. Illustrative parental combinations are shown in the table below.

TABLE 1

| | Diakaryon Combinations: | | |
|---|---|---|---|
| | | Parent 1 | Parent 2 |
| Phenotypes | requires | histidine | tryptophane |
| or | requires | arginine | lysine |
| or | requires | uracil | thymidine |

| | Trikaryon Combinations | | |
|---|---|---|---|
| | Parent 1 | Parent 2 | Parent 3 |
| Phenotypes requires and (provides fusion partners with) | histidine tryptophane (arginine) | tryptophane arginine (histidine) | arginine histidine (tryptophane) |

| | Tetrakaryons | | | |
|---|---|---|---|---|
| | Parent 1 | Parent 2 | Parent 3 | Parent 4 |
| Phenotypes requires and and (provides fusion partners with) | histidine tryptophane arginine (leucine) | tryptophane arginine leucine (histidine) | arginine leucine histidine (tryptophane) | leucine histidine tryptophane (arginine) |

As seen in the table, a variety of complementary characteristic/property combinations can be chosen to fit various fusion conditions. In general, the nutrient requirement is manifested by a mutant strain, while the ability to resist certain substances may more conveniently be conferred by modification of the nucleus with an expression system for the resistance gene. Alternatively, the nutritional requirement can be effected using recombinant techniques such as homologous recombination with a transforming vector and the resistance can be conferred by mutation under conditions where the toxic conditions are present.

In one embodiment of the invention, host cells are converted to spheroplasts for transformation. When spheroplasts are used, a preferred method or preparing them is by enzymatic digestion of the cell walls, for example, by using a chitinase/glutamase mixture. The selection of a suitable enzyme for enzymatic digestion is within the skill of the art. Useful enzymes are those capable of digesting complex polysaccharides, and are found among those known as effective in preparing fungal spheroplasts of a wide variety of fungal species. Specific examples of suitable enzymes include Novozyme 234 (an impure mixture of enzymes) and Beta-glucuronidase. Other suitable methods may be used to form spheroplasts. If suitable methods for cell wall penetration by the use of vectors are identified, however, whole cells of the fungal host may be used along with or instead of spheroplasts.

To modify the nucleus of a fungal host strain to contain am expression unit for a DNA encoding a particular subunit of multivalent vaccine, the practice of the invention employs, unless otherwise indicated, molecular biology, microbiology, and recombinant DNA techniques that is within the skill of the art. Such techniques are explained fully in the literature. See, e.g., Maniatis et al., Molecular Cloning: A Laboratory Manual (1982); D. N. Gover et al. DNA Cloning: A Practical Approach (1985) Volumes I and II; Oligonucleotide Synthesis (M. J. Gait ed. 1984); Nuclei Acid Hybridization (Hames et al. eds. 1985); Transcription and Translation (Hames et al. eds. 1984); Animal Cell Culture (R. I. Freshhey ed. 1986); Immobilized Cells and Enzymes (IRL Press 1986); B. Perbat, A Practical Guide to Molecular Cloning (1984).

General Procedure for Transformation of *N. crassa*

Once the population of DNA molecules encoding the multivalent antigens is placed into expression units, the DNA molecules are used to transform parent host strains of a filamentous fungus, such as described by Smart, "Heterologous dimeric proteins produced in heterokaryons." Strains of *Neurospora crassa*, are publicly available from the Fungal Genetics Stock Center, but independently prepares strains can also be used. Mutants may be isolated de novo, as illustrated by Stadler et al. Genetics (1966) 54:677-685 and Haas et al. Genetics (1952) 37:217-26. Useful strains can also be obtained from D. D. Perkins from Stanford University. Strains are typically grown on 1× Vogel's Minimal Medium ("N medium") in cotton-plugged test tubes, with appropriate supplements being added depending on the strain's phenotype.

Spheroplasts are used as subjects for transformation. To form conidial spheroplasts, the fungus is inoculated onto 25 ml of solid N medium, with appropriate supplements in four to five 125-ml Erlenmeyer flasks, which have been plugged with cotton. The cultures are grown at room temperature for 5-7 days.

The conidia are harvested by adding 10 ml of N medium to each flask, replacing the cotton plug, and swirling the flask. The solids are allowed to settle for a few minutes. The conidial mixture is poured to an autoclaved cheesecloth bag hanging in the mouth of an Erlenmeyer flask and secured with one or more rubber bands. The filtrate is recovered, and the concentration of conidia is determined by a hemocytometer count, with chains being counted as one.

A volume of $2 \times 10^9$ conidia is added to 150 ml of liquid N medium containing 1.5% sucrose and appropriate supplements. The conidia are germinated in the cotton-plugged flask while shaking (150-200 rpm) for 5-6 hours at room temperature until more than 75% have germinated and the germ tubes are 1-4 conidial diameters in length. The cells are harvested by centrifuging at about 1500-2000 rpm for 10 minutes. The cell pellet is rinsed three times with water.

The pellet is then re-suspended in 10 ml of 1.0M sorbitol, and the spheroplasts are prepared by enzymatic removal of the tough conidial cell wall with an enzyme under isotonic conditions, to prevent the "bursting" of the spheroplasts as they are formed. The protocol is adapted from the method of Vollmer and Yanofsky, Proc Natl Acad Sci USA (1986) 83:4869-73.

Specifically, in a sterile 250 ml Erlenmeyer flask, the conidial suspension is generally added to 50 mg of a solid enzyme sold by Interspex under the trade name Novozyme 234. The mixture is shaken (100 rpm) at 30° C. for about an hour (4±10 minutes) to digest the cell wall. The spheroplast formation process is monitored by examining a small aliquot of the mixture microscopically under a cover slip. Spheroplasts can be detected because they lyse osmotically when water is applied to one end of the cover slip. The process should be monitored frequently at the later stages of spheroplast formation.

The spheroplast mixture is decanted into a sterile 15-ml conical centrifuge tube, and the spheroplasts are recovered by centrifuging at 500 rpm (10 minutes) in a swinging bucket table top centrifuge. The resulting pellet is rinsed twice with 10 of 1.0M sorbitol and then once with the following STC solution: 91 g sorbitol; 50 mM Tris. Cl; 50 mM $CaCl_2$; sufficient NaOH to adjust the pH to 8.0; and q.s. to 500 ml.

The final spheroplast pellet is suspended in a mixture of 16.0 ml STC, 200 μl DMSO, and 4 ml of the following PTC solution: 200 g polyethylene glycol sold under the trade name "4000" by Sigma; 50 mM Tris. Cl; 50 mM $CaCl_2$; sufficient NaOH to adjust the pH to 8.0; and q.s. to 50 ml.

The resulting suspension of spheroplasts can either be used directly or stored frozen in 1.0 ml aliquots at −80° C.

In a sterile, 15-ml screw-cap tube, 2.0 μl of 50 mM Spermidine solution, 5.0 μl of the plasmid DNA to be transfected, such as that containing the expression system for an antigen of the desired multivalent vaccine along with a selectable marker such as benomyl resistance (usually at a concentration of about 1.0 mg/ml) and 5.0 μl of a 5 mg/ml heparin solution are mixed by flicking the tube. The spermidine solution is prepared by dissolving 12.73 mg of spermidine in 1.0 ml TE and adjusting the pH to 8.0, and can be stored at −20° C. The heparin solution is prepared by dissolving 50 mg of the sodium salt of heparin in 10 ml of STC and can be stored in frozen aliquots.

The contents of the tube are briefly spun (pulsed) in a tabletop centrifuge and then placed in an ice bath. About 50-100 μl of thawed spheroplasts are added to the tube. The mixture is then incubated on ice about 30 minutes, but incubation periods of about 20 minutes on ice have been successful. About 1 ml of PTC is added and mixed well by flicking the tube. The mixture is incubated further at room temperature for about 20 minutes.

A Regeneration "Top" Agar is prepared by mixing: 20 ml 50× Vogel's Minimal Medium; 825 ml of water; 182 g sorbitol; and 28 g agar. The top agar is autoclaved and 100 ml of a 10×FIGS. solution (containing 5 g/l fructose, 2 g/l inositol, 2 g/l glucose, and 200 sorbose) is added. 15 ml of the top agar is incubated at 50°-55° C. and poured into the tube containing the spheroplasts and plasmid DNA. The contents are quickly mixed by flicking and inverting the tube 2-3 times and then uniformly poured onto a layer of plating "bottom" agar.

The "bottom" agar is prepared by mixing any required supplements, in 1×N medium; autoclaving; and adding 10×FIGS. and benomyl (if benomyl resistance is used as a maker) to final concentrations of 1× and 0.5 μg/ml respectively. A volume of 25 ml of "bottom" agar is poured into a Petri plate and allowed to harden.

After the top agar has been poured over the bottom agar, bubbles are removed by flaming. The plates are kept in an upright position until the top agar has solidified (about 5 minutes). If the top agar tends to harden prematurely, the bottom agar plates can be prewarmed. Once the top agar has solidified, the plates are incubated in an inverted position at 30° C.

For selection of the *N. crassa* transformants, the host is thus cultured on the appropriate medium (having composition only the transformed cells can utilize or containing an antibiotic to which only transformed cells are resistant) and incubated at about 34° C. An indication of a successful transformation can be seen about 24-36 hours after plating. Stable transformants are generally scored after three days of growth. The incubation period to detect transformants will vary depending on the host strain and the phenotypic marker.

Selected transformants can be screened for, expression of the desired antigen subunit by standard methods, such as an appropriate ELISA, a colony blot immunoassay, restriction enzyme analysis, filter hybridization, nested deletion subcloning, and the like.

In the present invention, the above-described recombinant techniques are used to produce fungal host strains expressing a desired recombinant antigen or antigen group, each host strain having one or more characteristics that negatively affects growth under specified conditions but is correctable by a property conferred by a one or more other nuclei.

The resulting host strains are the parents used to form the heterokaryons of the invention.

Alternatively, electroporation procedures can be used to transform freshly harvested conidia of filamentous fungus such as *Neurospora crassa* (Van, D. C. Fungal Genetics Newsletter No. 42A (Supplement) (1995)). In general, conidia are harvested from 7-28 day old cultures. The cells are washed in 1 M sorbitol solution and suspended at a final concentration of 2.5×10⁹ cells/ml. Approximately 5 μg of linearized DNA is added to an aliquot of the conidial suspension and a portion of this is placed in the bottom of an electroporation cuvette, for example an electroporation cuvette with a 0.2 cm gap. An electroporator, such as an or a library of heterokaryons may be formed in a matrix using a microtiter plate or other convenient format. A few of the many combinations available are illustrated in the following table, Table 2, which is given by way of example and not meant to be limiting in any way.

TABLE 2

Generation of Heterokaryons For Production of Multivalent Vaccines

| Parent host cells contain genes from Influenza Strains with antigenic variants | AH1N1 a, b, c, ... | or | AH3N2 d, e, f, ... | or | BHN g, h, i, ... |
|---|---|---|---|---|---|
| A single vaccine production strain can be generated based on the choice of the user | | | | | |
| Heterokaryon comprised of: | strain c | plus | strain f | plus | strain h |
| Or a panel of vaccine production strains can be generated such as | | | | | |
| Heterokaryon one comprised of: | strain a | plus | strain d | plus | strain g |
| Heterokaryon two comprised of: | strain a | plus | strain e | plus | strain h |
| Heterokaryon three comprised of: | strain b | plus | strain f | plus | strain i |
| and so on in all possible combinations, if desired, | | | | | | where: 'A' = influenza type A; 'B' = influenza type B; 'H' = hemagglutinin; 'N' = neuraminidase; "variants" = different combinations of antigenc classes of H and N antigens of Influenza types and strains.

InVitrogen Electroporator II, is set with a voltage gradient of about 7.25 kb/cm and a setting of about 71 μF and about 200 ohms. Following electroporation, the cells are plated on appropriate media with or without a top agar essentially as described above.

Following transformation, a stable production strain derived form each molecular variant is established by expanding the culture on selective media for the particular host cell and expression unit used in each individual case.

Production of the Heterokaryon

Because all of the fungal host strains are chosen to be conallelic with respect to all heterokaryon compatibility alleles (with the exception of the mating allele when the tol gene is present as explained above), when the host strains are cultured together under conditions wherein none of the host strains can survive alone the fungi are fused so that the heterokaryotic fungus of the invention is formed. By hyphal fusion, the different haploid nuclei of the host fungi come to coexist in a common cytoplasm. While not wishing to be bound by any theory, applicants believe membrane fusion results from the aggregation of intramembranous particles within each cell, making possible cell contacts between protein-free areas. Rearrangement of the lipids in the contact areas then leads to full fusion.

Because each of the parents contains a nucleus which produces different antigens of the multivalent vaccine, the resulting heterokaryon is capable of producing the completed multivalent vaccine comprising multiple antigens.

The heterokaryon thus generated is stable, with the nuclei dividing at about the same rate.

Generation of Heterokaryons Producing Defined Multivalent Vaccines

The compositions and methods of the present invention employ heterokaryons expressing immunogenic antigens derived from pathogenic organisms. As described above, said heterokaryon is generated from two or more host strains, each heterokaryon producing a different multivalent vaccine.

One example is a heterokaryon that produces influenza antigen variants. To generate such a strain, conidial suspensions of each individual parent strain are mixed together on a solid media substrate without any nutritional supplements, or in the case of host cells with a resistance gene, in media containing the cytotoxic agent. A heterokaryon made from a predetermined combination of parent strains may be formed A typical minimal medium contains: per liter, 5.0 g Dextrose, 50.0 mls of a Salt Solution (below), 1.0 ml trace elements (below), and 12.5 g Agar (adjusted pH 6.5) if the media is to be in solid form. The Salt Solution contains: 120.0 g $NaNO_3$, 10.4 g KCl, 10.4 g $MgSO_4$, and 30.4 g $KH_2PO_4$.

The trace element solution contains: 1.1 g $(NH_4)_6Mo_7O_{24}.4H_2O$, 11.0 g $H_3BO_3$, 1.6 g $CoCl_26H_2O$, 1.6 g $CuSO_4$, 50.0 g $Na_2$ EDTA, 5.0 g $FeSO_4.7H_2O$, 5.0 g $MnCl_24H_2O$, and 22.0 g $ZnSO_47H_2O$ (pH 6.5).

Thus, to maintain the heterokaryotic filamentous fungus in its heterokaryotic state, external forcing is maintained. Growing the heterokaryotic fungal cells on minimal media "forces" the strains to remain together. If mating types are opposite, the presence of the tol gene can be used to maintain stable (A+a) heterokaryons.

The multivalent vaccine is produced by culturing the heterokaryons of the invention under conditions favorable to production of the antigens. The multivalent vaccine antigens may be recovered from the culture and purified in accordance with standard techniques adapted, of course, as necessary to preserve the structure of the antigens.

Preferably, the heterokaryotic filamentous fungus carries an expression unit that allows the host being cultured to secrete the desired multivalent vaccine directly into a minimal growth medium, so that the multivalent vaccine(s) can be purified directly from cell-free medium. Or the heterokaryotic filamentous fungus carries an expression unit that directs the antigens to the cell surface. Intracellularly produced multivalent antigens can be isolated from cell lysates. Useful purification methods in accordance with known procedures are within the skill of the art, such as, for example, molecular size exclusion, ion-exchange chromatography, HPLC, affinity chromatography, hydrophobic interaction chromatography, and the like.

Antigens

The disclosed invention is directed to the preparation of antigenic compositions, such as vaccines, against pathogens, particularly against pathogens that demonstrate the ability to change their antigenic character. Eucaryotic, viral, bacterial and fungal antigens are all contemplated for use with the described invention. Another use for the invention is to prepare antigenic compositions against a number of different antigens simultaneously. A preferred embodiment of the invention relates to the preparation of multivalent influenza vaccines. The influenza virus is constantly mutating and generating new strains. Accordingly, listing individual genes for use in the disclosed invention would be unnecessarily limiting as the invention is applicable to any influenza strain, or any pathogen strain for that matter.

There are three types of influenza virus, A, B and C. Types A and B viruses cause epidemics of disease almost every winter, while type C viruses only cause a mild respiratory illness and are not considered clinically important. Influenza type A viruses are divided into subtypes based on two proteins on the surface of the virus, the hemagglutinin (HA) and neuraminidase (NA). The current subtypes of influenza A viruses that infect humans are A (H1N1) and A (H3N2). There is currently a great deal or discussion about an avian influenza virus (H5N1) which is known to infect humans as well.

The influenza virus famously undergoes tremendous antigenic drift. A vast amount of effort is devoted around the world to monitor the antigenic drift of the virus, so that any new variant strains that arise can be identified and then used to produce updated vaccines which most closely match the strains likely to infect people in a given flu season. Upon identification of a strain of influenza of interest, the methods of the disclosed invention can be used to generate multivalent antigenic material which can then be used to prepare vaccines.

Another embodiment is directed to preparing multivalent vaccines against *Plasmodium*, a genus of protozoa that includes four species that cause malaria in human. Examples of the four include *Plasmodium vivax* and *Plasmodium falciparum*. A general list of pathogens against which multivalent vaccines are contemplated include human papilloma viruses 16, 18, and 31, human immunodeficiency virus (HIV) herpes varicella virus, measles virus, Epstein Barr virus, respiratory syncytial virus, parainfluenza 3, herpes simplex type 1 virus, and herpes simplex type 2 virus. Antigens suitable as targets for the disclosed invention include any protein from these organisms which is capable on eliciting an immune response in a host.

Assay for Secreted Antigens

Heterokaryon hosts can be stored on solid minimal media and also cultured on minimal liquid media under conditions favorable for expression of the multivalent antigens. Following 2-7 days of growth, the liquid media can then be collected under sterile conditions and tested for the presence of each specific desired antigen by standard analytical methods including but not limited to ELISA, PAGE, capillary electrophoresis, and spectrometry.

Upon identification of a culture that is producing the desirable variant of the multivalent vaccine, the cells stored on the solid media can be expanded to larger fermentation cultures by standard methods When grown under whatever the optimal conditions are for the particular fungal host used, this expanded host culture will produce the desired product is sufficient quantities for further research evaluation and eventual use as a recombinant vaccine.

Assay for Cell Surface Directed Antigens

Heterokaryons can be constructed that express fusion proteins that display the viral antigens on the surface of the fungal spore. Native proteins that are normally directed to the fungal cell surface, for example hydrophobin proteins, such as the EAS protein of *Neurospora*, as well as permease proteins, such as the MTR protein of *Neurospora*. These proteins are useful as cell surface-directed fusion partners with the viral antigens. Fusion proteins are constructed and expressed by means well know to practitioners of the art. Individual strains that express the antigen on the cell surface can be assayed by standard analytical methods. These methods include, but are not limited to, direct or indirect cell labeling by antibodies specific to the viral antigen, followed by detection of specific binding by various means. Such means include, but are not limited to, ELISA, visual or fluorescence spectrometry, and flow cytometry. Individual strains that express antigens may then be fused, are retested for simultaneous expression of the individually expressed surface antigens, and thus result in a multivalent target for the immune system, useful for recombinant vaccines, either directly or after purification.

Assay for Non-Secreted Antigens

If the antigens are not secreted, the cell mass in each liquid culture can be removed, disrupted by standard methods and the cell supernatant and debris assayed for the multivalent vaccine with desirable characteristics. Once the strain that produces the desired variant has been identified by standard methods, the strains stored on solid media can be used to inoculate and to make an expanded culture. Again, when grown under optimal conditions for the particular heterokaryon, this expanded host culture will produce the desired product in sufficient quantities for further evaluation and use.

The following examples are offered to illustrate but not to limit the invention.

Example 1

Synthetic HA Gene Constructs

Synthetic genes (HA0 of A/New Caledonial/20/1999/H1N1, HA of A/Vietnam/1194/2004/H5N1, and M1 of A/Vietnam/1194/2004/H5N1), were designed by the following method:

For each gene the amino-acid sequence was taken from the public NCBI database. In the HA and HA0 genes, a fungal signal sequence was substituted for the native leader sequence. Using this sequence, a gene for fungal expression was reverse-translated and codon-optimized using *Neurospora crassa* codon preferences. The sequence was altered to a low free-energy form, which was computed to reduce secondary structure in the nascent mRNA. The resulting gene was string-searched for intron splicing donor and acceptor sites. After alteration of the sequence to remove such sites, the sequence was also checked for transcriptional termination sites, and any fortuitous sites were removed.

The optimized sequence was then sequenced. The resulting DNA was subcloned into *E. coli* and then sequenced to check for errors in the synthesis. After sequence confirmation, the DNA was subcloned into an expression vector (pHDKXL1 for the HA and HA0 genes, pALGAM for the M1 gene), and transformed into *Neurospora*. The HA and HA0 genes were targeted for integration at the His-3 locus of *Neurospora*, and the M1 gene was targeted for integration at the Am gene of *Neurospora*.

Example 2

Expression of HA0 in *N. crassa*

An expression vector encoding the synthetic hemagglutinin 0 (HA0) gene with a fungal signal sequence attached to facilitate protein production was generated as discussed in Example 1.

Transformants were selected either for Histidine prototrophy (pHDKXL1/HA or HA0 transformants), or for Hygromycin B resistance (pALGAM/M1 transformants), using a host strain with a mutation at Histidine-3. After purification of the transformed strains by repeated streaking on selective medium, the transformants were screened for expression of the genes by ELISA. Secreted influenza antigens were detected in medium from shaker flasks. Flasks containing 25 ml of minimal Vogel salts plus 0.5% yeast extract in 125 ml Ehrlenmeyers were inoculated with approximately one million conidia spores/ml. Samples were either grown at 26 degrees C., shaking at 200 rpm, or in static culture at the same temperature. Samples taken after 2, 3, 4, 5, and 6 days of growth. The ELISA was developed using antibodies against influenza proteins, purchased from BIODESIGN. Control antigens used as standards were purchased from Protein Sciences Corporation. ELISA-positive samples were rescreened by Western blots using standard methods and reagents.

Various growth conditions were tested. Specifically, shaking and static cultures were specifically tested. Typically, the yeast was cultured for 2 to 6 days and samples were harvested for analysis.

Samples were fractionated by SDS-PAGE and blotted to nitrocellulose for imaging. Hemagglutinin was detected using a goat polyclonal anti-HA (H1N1) antibody, followed by anti-goat Ig-alkaline phosphate conjugate. Binding was measured by calorimetric detection.

Figure 8:
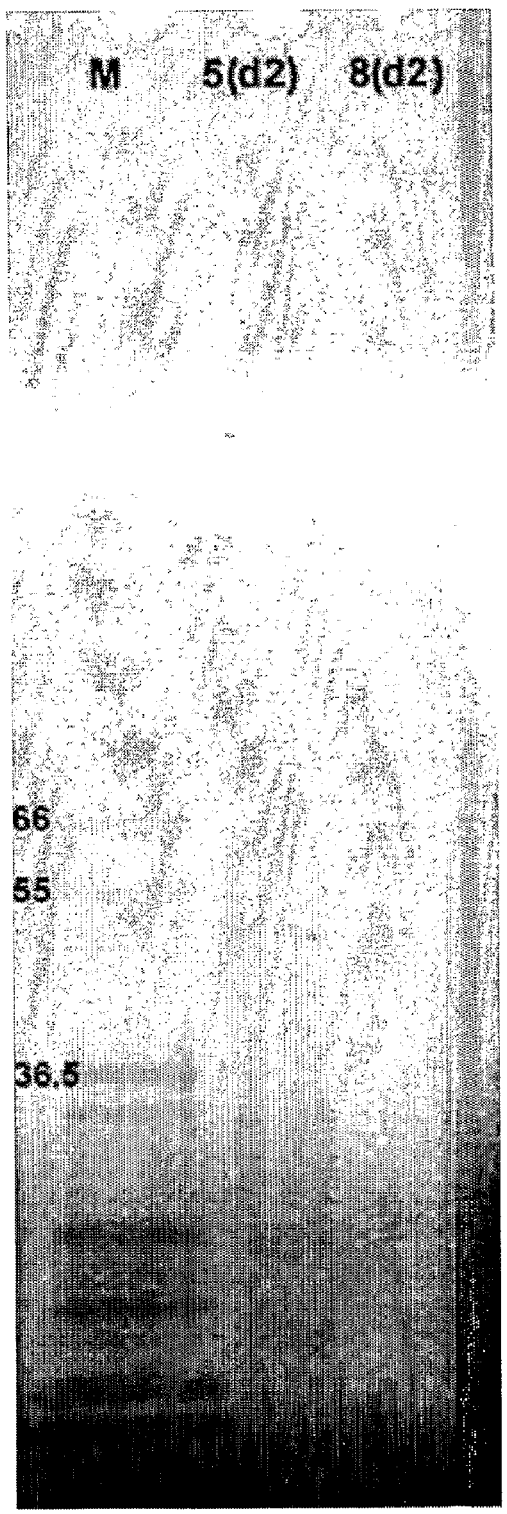
Figure 9:

A western blot detection of expression of the synthetic HA0 in *N. crassa* in FIG. 7. FIG. 8 shows a Coomassie blue stained SDS-PAGE gel from two different HA0 clones. FIG. 9 shows a western blot of static-culture expression of HA05. This data demonstrates the ability of the present system to recombinantly express influenza proteins in fungi.

Example 3

Multivalent Expression of Influenza Antigens in Fungal Heterokaryons

Expression vectors are prepared according to the method discussed in Example 1. The DNA is introduced into *Neurospora* by electroporation and transformants are selected according to the methods of Example 2. A multivalent mixture of influenza virus proteins is produced from the cultures since the expression vectors encode HA0, HA, and M1 matrix proteins.

The invention claimed is:

1. Filamentous fungal heterokaryons wherein said heterokaryons produce multivalent recombinant variants of antigens, said antigens comprise influenza type A and type B hemagglutinin and neuraminidase, said multivalent variants aggregate into particles that are secreted into the culture media, said heterokaryons are formed by fusing two or more fungal parent strains, said heterokaryons require the presence of all fungal parent nuclei for survival, said parent fungal strains each contains an exogenously supplied nucleic acid molecule that encodes a variant of said antigens, and said fungal parent strains are homozygous for all heterokaryon compatibility alleles.

2. The heterokaryons of claim 1 wherein each of said variants of influenza type A and type B hemagglutinin and neuraminidase is a naturally occurring variant.

3. The heterokaryons of claim 1 wherein each of said variants of influenza A and influenza B hemagglutinin and neuraminidase is not a naturally occurring variant.

4. A method to produce a multivalent vaccine, said method comprising the step of culturing the heterokaryons of claim 1 under conditions in which the exogenously supplied nucleic acid molecules are expressed so as to form a multivalent vaccine.

* * * * *